United States Patent [19]

Baskins et al.

[11] 4,323,777
[45] Apr. 6, 1982

[54] HYDROCARBON GAS ANALYZER

[75] Inventors: Lowell L. Baskins; Rodney M. Durham, both of Santa Barbara, Calif.

[73] Assignee: Infrared Industries, Inc., Santa Barbara, Calif.

[21] Appl. No.: 151,451

[22] Filed: May 19, 1980

[51] Int. Cl.³ ............................................ G01N 21/26
[52] U.S. Cl. ..................................... 250/339; 250/343
[58] Field of Search .............. 250/343, 344, 345, 346; 356/51, 432, 436, 437, 440

[56] References Cited

U.S. PATENT DOCUMENTS 4,059,356  11/1977  Kebabian ........................ 250/343 X

*Primary Examiner*—Davis L. Willis

*Attorney, Agent, or Firm*—George J. Netter

[57] ABSTRACT

A beam of infrared radiation encompassing the absorption band of the hydrocarbon alkanes is passed through an unconfined sample of test gas after which the beam is chopped before it impinges upon an interference filter. The filter restricts radiation passing therethrough to the spectral interval corresponding to the absorption band of the hydrocarbon alkanes. The filtered radiation impinges on an infrared detector which produces a signal that on being amplified, detected and demodulated is an analog signal of magnitude functionally related to the product of concentration and carbon number of the n-alkanes (flammability index) of a mixture of hydrocarbons irrespective of their individual carbon numbers. The apparatus is unitarily arranged in an elongated rod-like housing adapted for convenient hand-held use.

11 Claims, 5 Drawing Figures

HYDROCARBON GAS ANALYZER

The present invention relates generally to a hydrocarbon gas analyzer, and, more particularly, to such an analyzer providing rapid and accurate determination of the flammability index and toxic concentration of a gas sample composed of hydrocarbons having one or more alkanes as a principal constituent.

BACKGROUND AND PRIOR ART

Fuels derived from petroleum are customarily stored in very large quantities, and since they are flammable present a high hazard potential. Specifically, it is the hydrocarbon vapor-air mixtures of petroleum based fuels that are especially flammable, and which, if accidentally ignited, can produce explosions and costly fires. It is therefore manifest that apparatus for determining the presence and relative concentrations of hydrocarbon gases in a given area is a very useful item in preventing fires and explosions from that source.

It is well known that hydrocarbon vapors must be present in sufficient concentration to be flammable, and although various terms can be found in the literature to define this condition, the one which will be used here and which is commonly accepted in the industry at the present time, is "flammability index". Expressed in its simplest terms, the flammabilty index is the ratio of a measured hydrocarbon vapor concentration in air to the lowest concentration of the hydrocarbon in air that is flammable. That is, if the flammability index of a gaseous mixture is one or greater than one, the mixture is flammable. For all flammability index values less than one, the gaseous mixture is not flammable. It is clear that it would be a desiratum to determine quickly and easily not only the presence of hydrocarbon gases in a gas sample, but also whether or not these gases are in such concentration as to pose a risk of flammability, that is, whether the flammability index of the mixture is unity or greater than unity.

Although the risk of fire and explosion from the presence of concentrations of hydrocarbon vapors is a matter for great concern, it is not the only one. Even if hydrocarbon gases are present in concentrations below that necessary for flame propagation on contact with a source of ignition, they still may be present in such concentration as to make them injurious to the health or well-being of individuals in that environment. Accordingly, determination of this lower threshold limit in which human beings can remain on a continuous basis without adverse physical effect is also a very important matter. Since such toxic concentrations are well below those necessary to sustain flame propagation or burning, any apparatus which is to measure both flammability index and toxicity must have a correspondingly wide range of sensitivity to the hydrocarbon gases.

A known technique for determining the presence of combustible vapors and determining the flammability index of hydrocarbon based materials, such as, for example, gasoline, jet and diesel fuels, is frequently referred to as the catalytic oxidation principle. This technique involves burning a gas sample to be tested with the aid of a catalyst coated filament which is interconnected as one arm of a Wheatstone resistance bridge circuit. The temperature change of this filament resulting from the catalytic burning, unbalances the bridge providing an electric signal indicative of the concentration of the combustible materials (hydrocarbons) present in the sample. Although this approach has been widely used in the past, it is subject to a serious objection that it will not uniformly respond to all of the hydrocarbon constituents that may be present and, in particular, does not uniformly respond to alkanes, which are a principal constituent of the vapors of gasoline, jet and diesel fuels.

Another limitation of these catalytic devices is the necessity for providing a constant predetermined amount of oxygen in order to yield accurate results, since if either enriched or depleted oxygen atmospheres are used, erroneous readings and, in some cases, even complete failure of the instrument, can result. Still further in regard to these catalytic devices, it is necessary to transport the sample of the gas or vapor to be tested through a pipe or tubing to the sensing element which results in a certain amount of "hang-up" of the test vapor on the walls of the tube or fuel line, thereby providing an error in the determination since the material so hung-up does not take part in the catalytic burning. After a given measurement, hung-up molecules are not readily purged from the tubes, pipes or lines thereby possibly affecting accuracy of subsequent measurements.

There has also been developed a further approach for determining flammability utilizing a hydrogen flame ionization detector. It is basic to understanding of this approach to be aware that there is an orderly variation of the physical properties of the n-alkanes and, in particular, to understand that there is a substantially linear relationship of the carbon number of an alkane with the reciprocal of its lower flammability limit. The importance for present purposes of these interrelationships as they are applied to n-alkanes arises out of the fact that there is a preponderance of alkanes in petroleum-derived fuels and, of course, in their gaseous vapors.

In an article by Wilbur A. Affens and George W. McLaren entitled, "Flammability Properties of Hydrocarbon Solutions in Air", *Journal of Chemical and Engineering Data*, Volume 17, No. 4, 1972, the flammability properties of n-alkanes are described both as to vapor state and liquid fuel mixtures. Specifically, this article discusses combining Raoult's law and Dalton's law for a solution of a mixture of liquid hydrocarbons and Le Chatelier's rule for the flammability limits of vapor mixtures, for the purpose of attempting to predict the flammability index of a vapor mixture for arbitrary amounts of individual hydrocarbons.

In a further article by Wilbur A. Affens, Homer W. Carhart and George W. McLaren entitled, "Determination of Flammability Index of Hydrocarbon Fuels by Means of a Hydrogen Flame Ionization Detector", *Journal of Fire and Flammability*, Volume 8, 141 (April, 1977), a hydrogen flame ionization detector for measuring the flammability index of vapor-air mixtures is described. In this article, the response of the instrument is shown to be proportional to the concentration and the number of carbon atoms in the molecules of the constituent gases. Although this instrument offers some advantages over the prior referenced catalytic oxidation devices, it has some significant disadvantages, the chief one being that for proper operation it requires certain optimum flow rates of the gases for the instrument blend of the hydrocarbon and nitrogen. In addition, the described apparatus has a slow response to heavy or high carbon number hydrocarbons. It is doubtful that such a device could be made portable at a moderate cost. Still further, it is necessary to transport the sampled gas along a tube or pipeline of some kind which runs the risk of adsorbed hydrocarbon vapors or liquid fuel (hang-up), as the case may be, adding a substantial error especially when measuring relatively low concentrations of hydrocarbons for toxicity determinations.

OBJECTS AND SUMMARY OF THE INVENTION

It is therefore an object of the present invention to provide improved apparatus for measuring the flammability index of hydrocarbon gases of unknown hydrocarbon constituents or mixtures thereof.

A further object is to provide apparatus in accordance with the previous object for indicating relatively low level concentrations of hydrocarbon gases and thereby the presence or the toxic hazard presented by a given sample thereof.

Another object is the provision of apparatus for providing a direct readout of the flammability index and toxicity of a sample of hydrocarbon gases having alkanes as a primary constituent.

Yet another object of this invention is to provide such flammability index and toxicity measuring apparatus that is substantially unaffected by normally encountered variations of the gas sample temperature.

Another object is the provision of apparatus as in the above objects, that substantially eliminates gas sample hang-up.

A still further object of the invention is to provide flammability index and toxicity measuring apparatus for hydrocarbons in which calibration can be made for the instrument to give a single readout for mixtures of n-alkanes in the gas sample.

In the practice of the present invention, there is provided a gas analyzing apparatus, including a source of infrared radiation encompassing the absorption band of the hydrocarbon alkanes. Radiant energy from the infrared source is passed through an open unconfined sample of the gas to be tested after which the radiation beam is interrupted by a vibrating reed before it impinges upon an interference filter. The filter restricts radiation passing therethrough to the spectral interval corresponding to the absorption band of the hydrocarbon alkanes except methane.

The filtered radiation is directed onto an infrared light detector which produces a signal that on being amplified, detected and demodulated is an analog signal of magnitude functionally related to the product of concentration and carbon numbr of the n-alkanes or, more particularly, the flammability index of a mixture of hydrocarbons irrespective of their individual carbon numbers. The analog output (which, optionally, may be linearized) is displayed on a meter or other suitable display or recording device.

The described apparatus is unitarily arranged in an elongated rod-like housing adapted for convenient hand-held use. The infrared radiation source is at one end of the housing and an elongated chamber in communication with the beam source has a plurality of slots in the chamber wall such that the ambient atmosphere can readily make its way into the chamber forming an unconfined gas sample to be tested. The vibrating reed, interference filter and infrared detector are located to receive the infrared beam after it has passed through the gas sample. A power pack is separately provided which can be carried by a handle or, optionally, by a shoulder harness.

DESCRIPTION OF A PREFERRED EMBODIMENT

Figure 1:
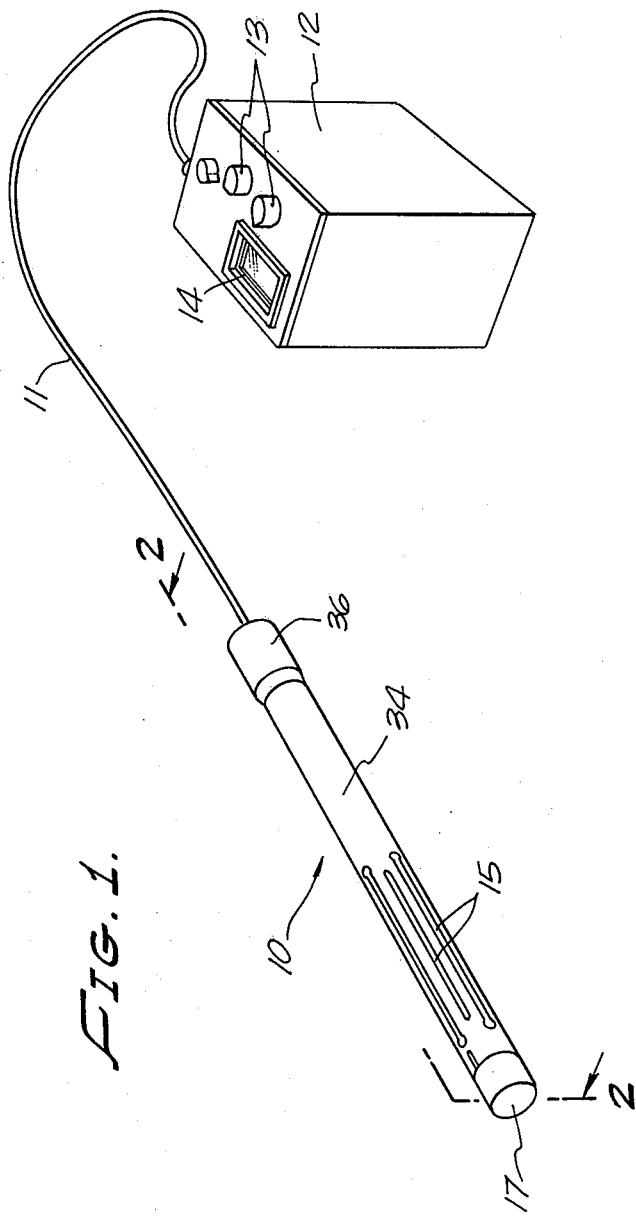
FIG. 1 is a perspective view of one form of gas analyzer of this invention shown in portable form with power supply.

Turning now to the drawing and particularly FIG. 1, the gas analyzer of this invention is seen to include in its major aspects, an elongated, generally cylindrical probe 10 adapted for hand-held use and being of such weight and dimensions as to permit its being readily carried and manipulated as desired or needed. A flexible cable 11 interconnects the probe with a separate source of electric power 12, the latter also including calibration and adjusting controls 13 as well as a display 14 for direct readout of determinations. Broadly as to use, the operator of the equipment can carry the power supply by a handle or other conventional means, such as a shoulder harness, for example, and after suitable calibration merely locates the end of the analyzer probe 10 in the region containing gas sample to be tested, with determinations of flammability index and toxicity (i.e., concentrations indicating toxicity) being immediately indicated on the display 14. As will be more definitively described, the analyzer tests a gas sample which is relatively unconfined, the ambient atmosphere of the probe passing freely through a set of elongated slots 15 into an open test chamber within the probe and thereby forming the gas sample.

Figure 2:
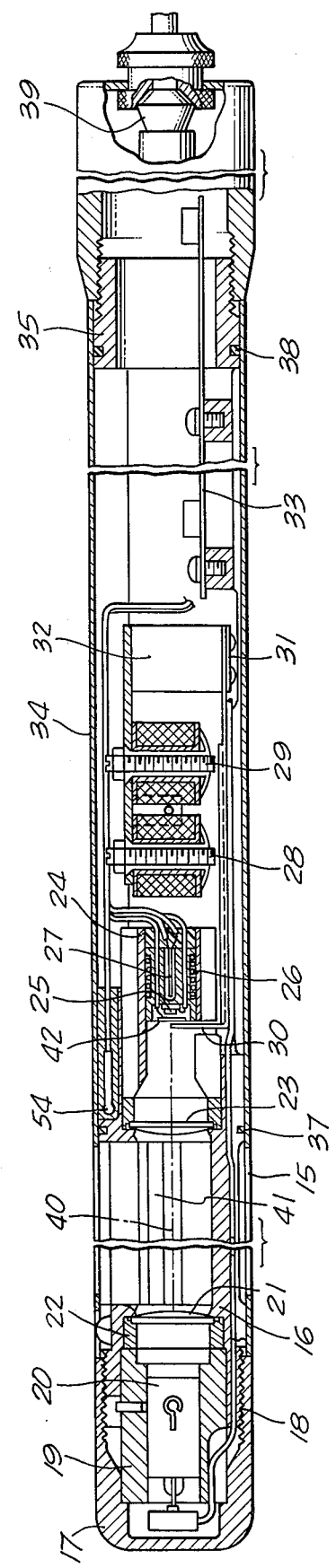
FIG. 2 is a sectional, elevational partially fragmentary view taken along the line 2—2 of FIG. 1.

Turning now to FIG. 2 showing the probe assembly 10 in section, the probe housing 16 is a casting which forms the skeletal structure of the probe. The outermost end of the probe 10 includes a cup-shaped bell or cap 17 with a threaded open end 18 which is received onto a similarly threaded end of the housing casting. The cap also encloses a further housing 19 which, in turn, contains a radiation source 20. This source module is keyed to insure a fixed predetermined orientation in the probe. A first focusing lens 21 is secured to an annular retainer 22 which is bonded to the probe housing. The length of the probe casting which forms the test chamber has a plurality of slots 15 which allow the ambient gases to readily enter the measurement chamber. The chamber extends from the first focusing lens 21 to a second focusing lens 23 with the respective lens assemblies being secured to the probe casting to maintain precise alignment. Further down the probe housing and behind the second focusing lens 23 is located an insulative housing 24 which includes an infrared detector 25 and electric heater 26.

The detector 25 is positioned so that the first focusing lens 21 and second lens 23 focus the infrared radiation from 20 directly onto the detector. In a way that will be described, the heater 26 coacts with a temperature monitoring means 27 to maintain the detector at a predetermined temperature thereby obviating measurement errors resulting from temperature variations of the detector.

Beyond and outside the insulative detector chamber or housing 24, there are provided a pair of electromagnets 28 and 29, the cores of which are arranged transversely of the probe longitudinal axis, in parallel relation to each other and with their ends substantially coplanar. An elongated L-shaped armature 30 has one end affixed as at 31 to a common base 32 with the electromagnets.

The cross-arm end of 30 extends transversely of the infrared sensitive detector 25 and in the power off state rests in the radiation beam partially attenuating the signal. When power is applied, the electromagnets are energized, this attracts the L-shaped member toward the electromagnets causing the cross-arm to interrupt or block the radiation beam. The signal which is generated shuts off the electromagnet and the L-shaped member or reed springs back out of the beam. The resulting signal change turns on the electromagnet and draws the reed back across the beam, thus causing the reed to oscillate at its natural frequency. This oscillating reed "chops" the radiation beam so that the radiation detector receives a pulsating signal. The output of the detector is, therefore, an AC signal which is more readily electronically processed. Within the structure of the probe housing includes a circuit board illustrated schematically as at 33, which includes electrical circuits for amplifying the detector output signal, regulating the detector and spectral filter temperature, and driving the electromagnets.

An elongated hollow metal tube 34 is received over the probe housing and extends from the end of the test chamber at the second focusing lens 21 to the threaded end 35 of the probe housing which mates to the handle 36. The hollow tube is sealed at each end with O-rings 37 and 38. The handle 36 has an opening and end sealing grommet 39 through which the cable 11 passes for interconnection with the control box assembly to be described.

It will be noted that with the exception of the test chamber between the lenses 21 and 23, the probe parts are substantially sealed from ambient atmosphere by O-rings at 37 and 38, the sealing grommet 39, and the bonded lenses 21 and 23, themselves. This insures against the access of ambient gases into the interior with possible undesirable results of either erroneous operation of the equipment or damage to the electrical components.

Furthermore, it will be noted that in order to protect against the ignition of a flammable atmosphere, spark-free operation has been assured in construction of the radiation chopping mechanism. The radiation source filament is sealed in a glass chamber which is then enclosed in an aluminum chamber. The electrical current to the probe assembly is limited in the control box assembly. The rugged aluminum probe housing also provides good strength and mechanical integrity.

Briefly as to the general operation of the apparatus described to this point, the radiation source 20 directs an infrared beam along the probe axis 40 to pass through the gas sample in the space 41 made available through the slots 15. Assuming the presence of gaseous materials of the kind for which the described instrument has been constructed are present in the gas sample, certain predetermined frequency ranges of light will be absorbed by the sample and the remainder will pass through to be focused by lens assembly 23 onto the detector 25. The movement of the interrupting armature or chopper 30 responsive to energization of the electromagnets 28 and 29 causes the detector to produce an alternating electric output signal responsive to the pulsating light received through the gas sample. The circuits 33 of the circuit board and those in the control box process the alternating signal rendering an analog signal having a value indicative of the concentration of the specific gaseous material existing in the sample.

The probe assembly 10 is connected to the control box assembly 12 via interconnect cable 11. The control box assembly houses the battery, calibration and adjusting controls 13, display 14 and the final processing electronics circuit board. The control box circuit board rectifies the alternating signal received from the probe assembly, applies an appropriate span gain and corrects for variations in gas temperature. The battery charger circuit, audible alarm and recorder output are also located in the control box.

Since the filter 42 located between the lens assembly 23 and detector 25 has been selected to pass radiant energy having a bandwidth of 170 wavenumbers centered at 2920 wavenumbers, the described apparatus provides a signal corresponding to the flammability index of alkanes in the gas sample and does so irrespective of the type of alkanes or their relative concentrations. That is, whatever the various relative mixtures of alkanes are in the gas sample being tested, with the filter of the prescribed physical characteristics, the flammability index of that mixture or any other mixture of alkanes will be accurately represented by the analog output of the circuit apparatus 33.

In use of a practical construction of the gas analyzer described herein, it has been shown that if the concentration of a given alkane is normalized to its lower flammability limit, the response of the described equipment is described by the same equation parameters and thus this equipment will respond substantially the same for all alkanes, except for methane. In explanation of this, denoting the attenuation of radiant energy along the sample path by A, the response for any single selected alkane is given by $$A = F[1 - \exp\{-\beta KE/(1 + 2KE)^{\frac{1}{2}}\}]$$

where $K$ and $\beta$ are fixed parameters relating to the physical properties of the spectral lines which have been assumed in the two-parameter spectral band absorption model given by R. N. Goody in the *Quarterly Journal of the Royal Meteorological Society*, Volume 78, 165 (1952). Also, the particular spectral interval chosen for the instrument, E, is equal to the fractional or molar concentration of the alkane vapor divided by its lower flammability limit, and F is a calibration constant to correct for slight deviations from the gas model suggested by Goody. The flammability index for the mixture of gases is considered to be equal to the sum of the flammability indices of the components as suggested by Affens et al in the earlier referenced article. For alkane mixtures which specifically occur in gasoline, jet and diesel fuels, it has been established through use of the described equipment that a good approximation of the attenuation A is obtained by equating E to the sum of the respective flammability indices such that E can be considered the total flammability index for the mixture. As indicated, methane, as well as certain unsaturated hydrocarbons, are exceptions and the instrument response for these will be considerably less than that indicated by the equation. However, it has been found in practice that the effect of unsaturated hydrocarbons or methane in the vapors of hydrocarbon fuels is relatively insignificant, because these components are relatively small at ordinary temperatures.

Figure 3:
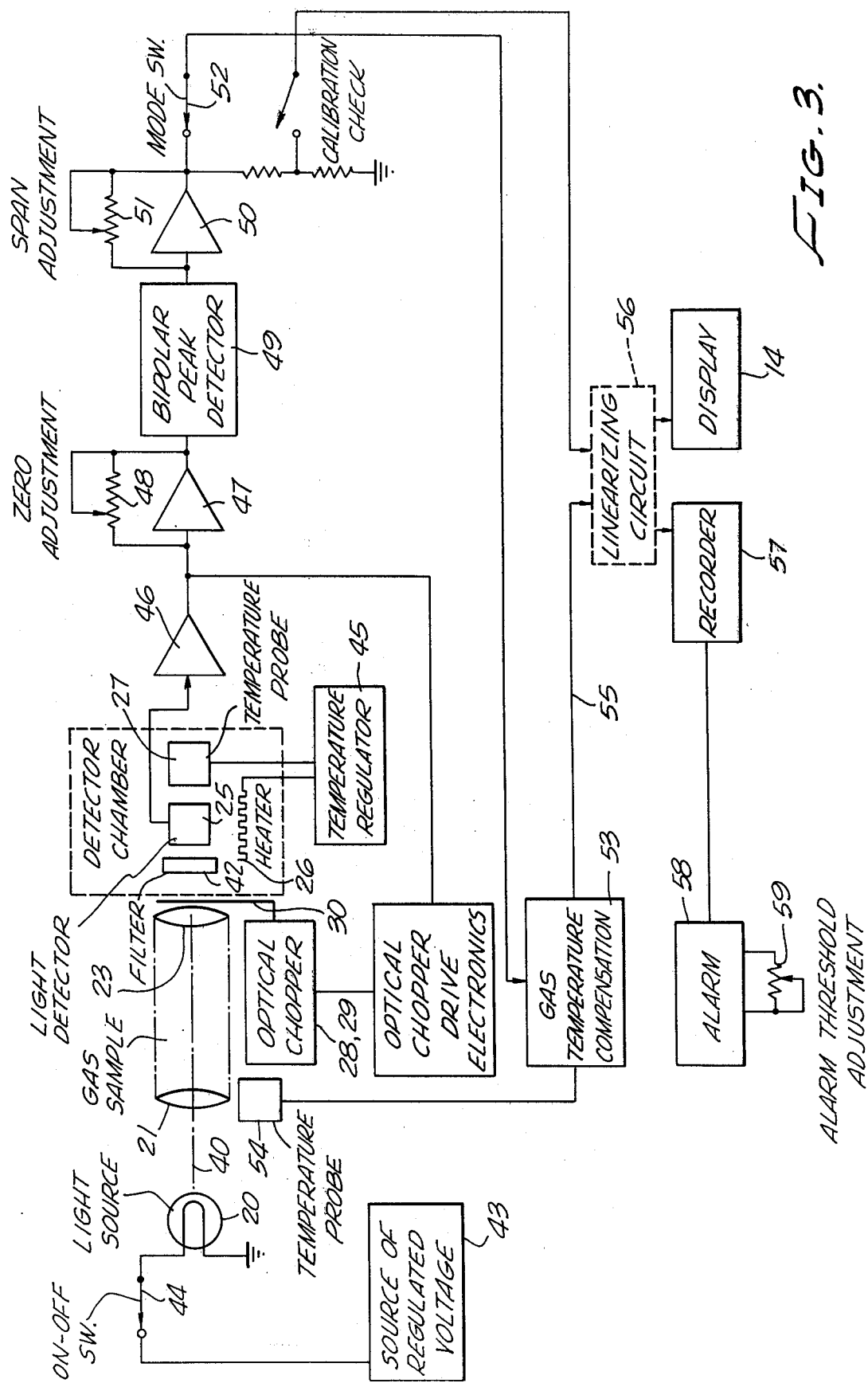
FIG. 3 is a function block circuit schematic of the gas analyzer of this invention.

Turning now to the circuit schematic of FIG. 3, a detailed discussion of operation of the invention for a given gas sample will now be given. The radiant source 20 is energized by a source of regulated voltage 43 in the portable power supply 12 via an on-off switch 44 providing selective control to produce a beam of infrared energy directed along 40. The lens 21 focuses the infrared beam to pass through the sample of gas, the index of flammability and toxicity of which is to be determined. The optical chopper (i.e., armature 30) interrupts the infrared beam from the lens assembly 23 transforming it to a cyclically pulsating beam impinging on filter 42.

The interference filter 42 transmits infrared energy in a preselected relatively narrow band which includes the absorption band of the gas in interest. For the case of n-alkanes, excluding methane, the filter is selected to transmit radiation in a narrow band centered at 2920 wavenumbers which encompasses the absorption band of the alkanes. The filtered, pulsating infrared energy impinges upon the detector 25 producing an alternating electric signal output. In a practical construction of the invention, a lead selenide (PbSe) photodetector was used which has been found to have excellent response to a wide range of infrared radiation. The detector housing 24 is maintained at a predetermined temperature (approximately 60° C.) by closed loop operation of the temperature probe 27, temperature control circuit 45 and heater 26. The temperature control of the detector chamber is important in substantially eliminating errors resulting from temperature changes of the detector 25.

The signal from the detector is preamplified at 46, a portion of which output is amplified to drive the optical chopper electromagnets 28 and 29. The preamplified signal is also fed into a further amplifier 47 where it can be scaled by a zero adjustment resistor 48 to set the zero level. Zero level physically corresponds to the signal amplitude existing when there is no gas in the sample chamber to absorb infrared energy in the spectral region passed by the interference filter 42.

After rectification in the bipolar peak detector 49, the signal from amplifier 47 is further amplified as at 50 to an extent determined by the adjustment position of span adjustment resistor 51. The span adjustment controls the gain of the amplifier and thus enables scaling the signal to correspond to the appropriate meter deflection for a given gas measurement.

Since the described equipment is actually responsive to the gas density within the sample cell, temperature and pressure of these gases can strongly influence the measurements taken. It has been found that atmospheric pressure changes are, for the most part, of negligible effect in the course of any given set of measurements of flammability index or toxic level. Temperature changes, however, can be considerable so that provision has been made in the circuit to compensate for gas temperature variation on the output signal. In the normal operating mode, the switch 52 is closed which passes a signal to a gas temperature compensation circuit 53 having its amplification under the control of a temperature sensing probe 54, the latter being located closely adjacent to and in thermal contact with the gas sample.

The output of the gas temperature compensation circuit is a DC analog 55 having a magnitude functionally related to the filtered light impinging on the detector 25, and thus to the concentration of n-alkane hydrocarbons in the gas sample. The analog signal does not vary linearly with gas concentration, and if linearity of display or recording is desired, a linearizing circuit 56 of known character may be optionally employed. Display may be accomplished by the meter 14 (FIG. 1) or any other suitable known display means. Similarly, there may be optionally provided a recorder 57 such as a pen recorder or any one of a number of other available recording devices. A selectively adjustable alarm 58 (e.g., light, buzzer, tone) is also optionally provided to give an indication when a predetermined concentration level is measured by the equipment.

Prior to taking actual measurements, the described gas analyzer should be calibrated to insure accuracy. The various control knobs 13 are manipulatable to switch electrical parts of the system in a way that will now be discussed in some detail to establish proper calibration. First, one of the knob controls is set to "Battery Check" which interconnects the DC power supply to the meter display 14 via a suitable resistance network, and if the power supply has an adequate output, the display 14 will indicate this. This is a conventional matter and therefore has not been shown in the circuit schematic of FIG. 3.

When the controls are set to a position termed "Check", the switch 44 disconnects the infrared source which the equipment reacts to as if all of the infrared energy had been absorbed by the gas sample. The resulting signal is scaled to register a full scale deflection on the meter display 14.

Next, the control switches are set to a position termed "Standby" which energizes the electric heater 26 to bring the detector chamber or housing 24 up to the desired 60° C. This is important, as has already been noted, to eliminate possible errors from temperature variations of the detector 25.

An "Alarm Set" position of one of the control knobs allows adjustment of the alarm threshold resistor 59 so that the alarm will be actuated when a given minimum value is exceeded on the display 14.

A "Zero Control" potentiometer (i.e., resistor 48) enables setting the zero on the display meter.

With respect to the making of toxicity measurements by the present invention, the measurements made and indicated on the display 14 are still those of alkane concentration. The dial face of the display 14 can be marked so as to indicate whether or not the given alkane concentration is dangerous to humans or not. The determination of what the safe concentration levels of a given alkane are, are beyond the scope of the present writing, it is merely necessary for use of the present invention for toxicity measurements to know that maximum safe levels have been determined by others. For example, OSHA published in 1978 the following maximum concentrations of the indicated alkanes that could be safely tolerated by a human on a continuous basis:

| Hydrocarbon | Parts Per Million (ppm) | Flammability Index |
|---|---|---|
| Heptane | 500 | .049 |

-continued

| Hydrocarbon | Parts Per Million (ppm) | Flammability Index |
|---|---|---|
| Hexane | 500 | .042 |
| Octane | 500 | .056 |
| Pentane | 500 | .036 |
| Propane | 1000 | .042 |

Figure 4:
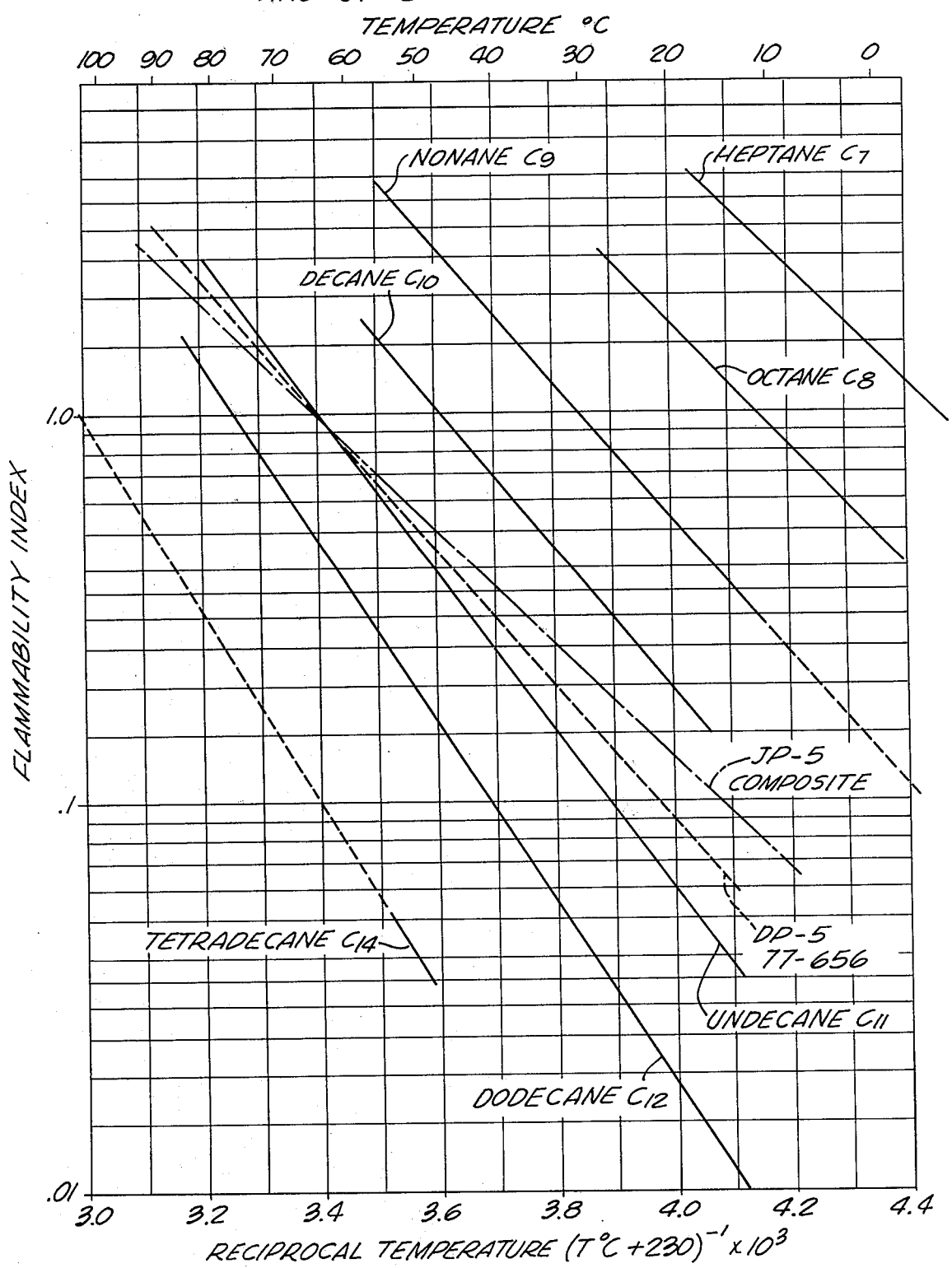
FIG. 4 is a graph of flammability index measurements performed in accordance with the practice of this invention.

Turning now to FIG. 4, there is shown there the results of a number of test runs made with a practical construction operating on the principles of this invention. The following table has been prepared comparing published flash points (i.e., flammability index 1.0) with the actual measurements of FIG. 1:

| Hydrocarbon | Carbon No. | Flammability Index = 1.0 From Figure 4 | PUBLISHED DATA Literature Average | Calculated (Graphical) | Calculated From Equation* | Experimental Tag Closed Cup** |
|---|---|---|---|---|---|---|
| Heptane | 7 | −5.4° C. | −3 | −6 | −7 | −1 |
| Octane | 8 | 11.0 | 14 | 13 | 11 | 15 |
| Nonane | 9 | 30.1 | 31 | 31 | 29 | 33 |
| Decane | 10 | 46.8 | 46 | 47 | 45 | 48 |
| Undecane | 11 | 64.1 | 64 | 62 | 61 | 64 |
| Dodecane | 12 | 76.7 | 74 | 76 | 76 | 79 |
| Tetradecane | 14 | (104.0) | 107 | 103 | 104 | — |

*$(t_F + 277.3)^2 = 10410 \, n$.
**The Tag Closed Cup Testor is a standard method of test, ASTM Designation: D56-70.

It is readily apparent that actual measurements made correspond quite closely to the expected values as obtained from published materials.

Figure 5:
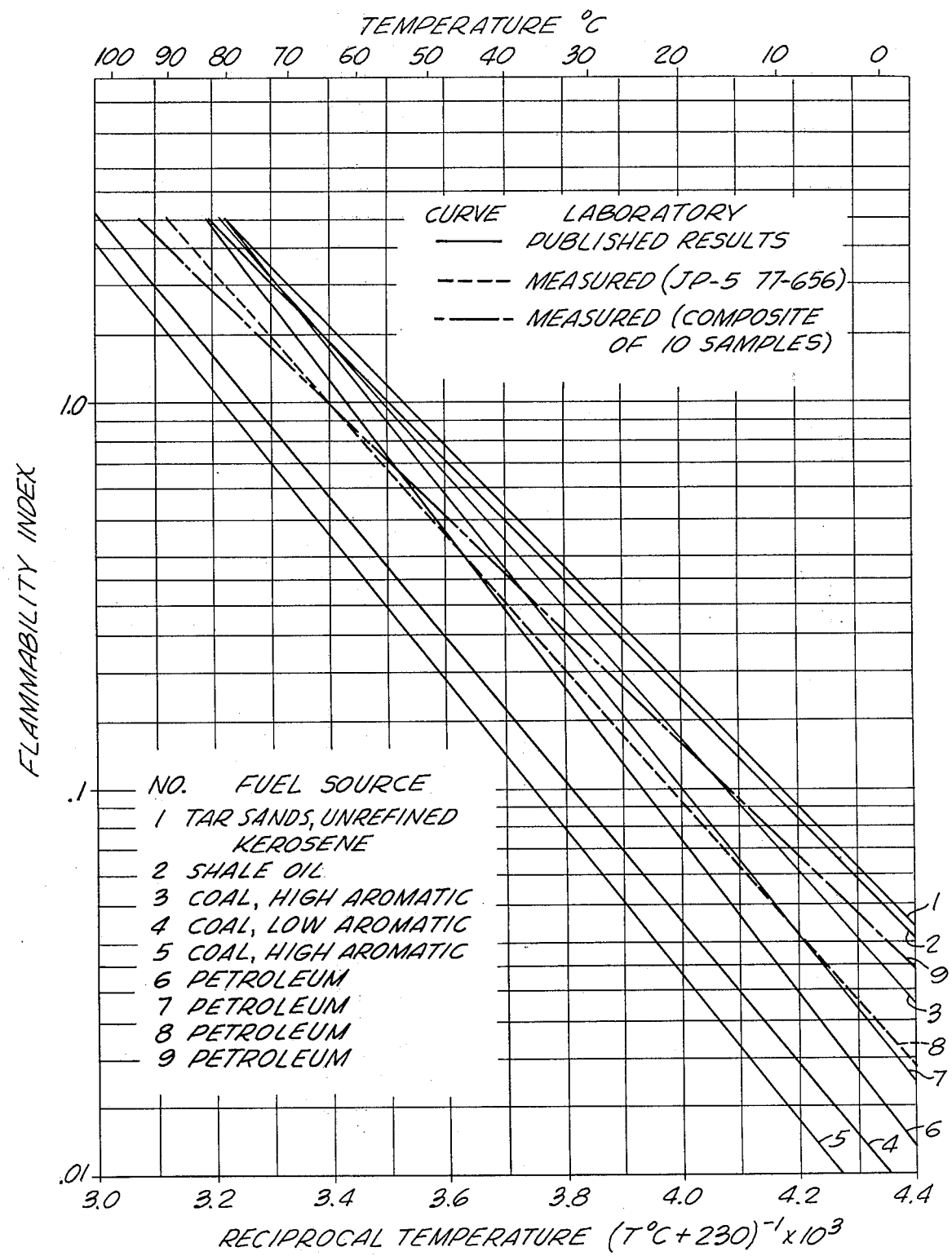
FIG. 5 is a graph depicting flammability index measurements taken in accordance with this invention as compared with measurements taken by standard laboratory techniques.

FIG. 5 shows flammability indices of a jet fuel referred to generally as "JP-5", the fuel samples being obtained from a variety of different source materials, as identified. The measurements taken by a practical construction employing the principles of this invention are believed to be sufficiently close to measurements taken by the Naval Research Laboratory employing conventional techniques, as to establish that the measurement of flammability indices of JP-5 by the present invention are satisfactory for the full range from substantially less than 0.01 to well above 1.0.

Although a primary utility of the described apparatus is determination of flammability indices of hydrocarbon vapors, and secondarily the determination of the presence of hydrocarbons in such concentration as to present a toxic danger to humans, there are other and different uses to which the apparatus may be put. For example, it may be desirable under certain circumstances to detect the mere presence of hydrocarbons in a gas sample without regard to any quantitative evaluation, and the apparatus described herein may be used directly for that purpose with perhaps use of a different display means. Also, the apparatus can be readily adapted to detect a specific hydrocarbon, or specific set of hydrocarbons, by changing the filter and modifying the electronics appropriately.

A further application of the portable hydrocarbon analyzer is in the field of arson investigation. It is important for the investigators to locate, within a reasonably short period of time, those areas in the burned building under investigation, where gasoline, kerosene, or other accelerants may have been present, and, therefore, may have been used by an arsonist. Current methods for locating these vapors include the use of "hot wire" type combustibles analyzers. These analyzers have a response to alkanes which falls off with increasing carbon number. Also, the response of a hot wire analyzer to hydrocarbon fuel vapors such as gasoline or kerosene is limited. The greater sensitivity of the portable hydrocarbon analyzer described herein would be a significant advantage for this purpose.

As already noted, the described apparatus has excluded methane since this lightest member of the alkane family does not behave in the orderly manner of the other alkanes allowing its flammability index to be added in a linear manner to that of other alkanes in a gas mixture to obtain the flammability index of the mixture. The absorption band of methane is centered at 3020 wavenumbers which is somewhat higher in frequency than the band typical of other alkanes. The apparatus may be modified to be more responsive to methane by changing the spectral filter 42 to one centered at 3020 wavenumbers and changing the gains appropriately in the preamplifier 46 and span amplifier 50 to correspond to the change in the signal strength and signal modulation resulting from the presence of methane gas. The apparatus set up in this manner would not have the property of being responsive equally to different alkane gases of the same flammability index, but would, instead, be set up specifically for methane and typically calibrated for a full scale response on high range of 5% methane which is a flammability index of 1.0. In use, the instrument so adapted could be advantageously employed for monitoring the presence of methane in mines or in and around fuel storage tanks.

What is claimed is:

1. Apparatus for determining the flammability index of hydrocarbon fuel vapors, comprising:
    an infrared energy source for directing infrared energy therefrom along a predetermined path;
    means for holding a sample of the fuel vapors in said path;
    a filter located in the path to receive the infrared energy from said sample, said filter passing a range of infrared energy therethrough substantially corresponding to the absorption band of alkanes;
    means responsive to the filtered infrared energy for generating a signal functionally related to the concentration of alkanes in the gas sample; and
    temperature sensing means in thermal communicating relationship with the gas sample; and
    means actuated by said temperature sensing means to compensate the signal for changes in gas sample temperature.

2. Apparatus as in claim 1, in which there are further provided means responsive to said signal for displaying gas sample concentration.

3. Apparatus as in claim 1, in which said means for holding the sample includes a tubular member having wall openings in open communication with the ambient atmosphere.

4. Apparatus as in either of claims 2 or 3, in which the source of infrared radiation, means for holding the gas sample and signal generating means are unitarily mounted in a cylindrical housing and adapted for hand-held use.

5. Apparatus as in claim 1, in which the means responsive to the filtered infrared energy includes an infrared radiation detector and means for maintaining the temperature of said detector at approximately 60° C. during use.

6. Apparatus as in claim 1, in which said filter is an interference filter centered at approximately 2920 wavenumbers.

7. Apparatus as in claim 1, in which said filter is an interference filter centered at approximately 3020 wavenumbers for detecting and measuring methane.

8. Apparatus as in claim 1, in which said filter is an interference filter centered at the absorption peak of a particular hydrocarbon, said peak lying in the range of about 2800 to 3200 wavenumbers.

9. Apparatus for determining the flammability of a hydrocarbon vapor sample including one or more alkanes other than methane as components thereof where the flammability index of each such alkane is $E1, E2 \ldots En$, comprising:
- a source of infrared radiation encompassing the absorption band of all alkanes other than methane;
- a chamber for containing the hydrocarbon vapor sample;
- means for directing the infrared radiation from said source onto the gas sample in the chamber;
- an interference filter positioned to receive infrared radiation after it has passed through the gas sample in the chamber, said filter passing all radiation lying within substantially the entire absorption band of the alkanes and restricting passage of radiation outside said band; and
- means substantially uniformly responsive to radiation throughout said alkanes absorption band for providing an electric signal generally proportional to the sum of the flammability indices $E = E1 + E2 \ldots En$ of the vapor sample.

10. Apparatus for determining the presence and relative concentration of a hydrocarbon fuel vapor in a gas sample, comprising:
- means for directing a quantity of infrared radiation onto said gas sample;
- a filter located to receive the infrared radiation from the gas sample, said filter centered at approximately 2920 wavenumbers and having a spectral width of approximately 170 wavenumbers;
- means responsive to the filtered infrared radiation for generating an electric signal generally proportional to the quantity of filtered radiation; and
- a display driven by said responsive means for providing an indication of the presence of a hydrocarbon in a concentration above about 10 parts per million.

11. Apparatus as in claim 10, in which said means responsive to the filtered infrared radiation includes an infrared radiation detector and heating means for maintaining said detector at an elevated preselected temperature.

* * * * *